(12) United States Patent
Tournier-Lasserve et al.

(10) Patent No.: US 7,364,844 B1
(45) Date of Patent: Apr. 29, 2008

(54) **USE OF THE *KRIT1* GENE IN THE FIELD OF ANGIOGENESIS**

(75) Inventors: Elisabeth Tournier-Lasserve, Paris (FR); Sophie Laberge-Le-Couteulx, Rouen (FR); Pierre Labauge, Montpellier (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1113 days.

(21) Appl. No.: 10/019,434

(22) PCT Filed: Jul. 3, 2000

(86) PCT No.: PCT/FR00/01887

§ 371 (c)(1),
(2), (4) Date: May 7, 2002

(87) PCT Pub. No.: WO01/02604

PCT Pub. Date: Jan. 11, 2001

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ............. None
See application file for complete search history.

(56) References Cited

OTHER PUBLICATIONS

Serebriiskii, I. et al., "Association of Krev-1/rap1a with Krit1, a novel ankyrin repeat-containing protein encoded by gene mappin to 7q21-22", Oncogene, vol. 15, pp. 1043-1049 (1997).*

Bergametti, F. et al., "Mutations within the Programmed Cell Death 10 Gene Cause Cerebral Cavernous Malformations", Am. J. Hum. Genet., vol. 76, pp. 42-51 (2005).*

Cave-Riant, F. et al., "Spectrum and expression analysis of KRIT1 mutations in 121 consecutive and unrelated patients with Cerebral Cavernous Malformations", Eur. J. Hum. Genet., vol. 10, pp. 733-740 (2002).*

Lucas, M. et al., "Variable expression of cerebral cavernous malformations in carriers of premature termination codon in exon 17 of the Krit1 gene", BMC Neurology, vol. 3, pp. 1-6 (2003).*

Reich, P. et al., "Molecular genetic investigations in the CCM1 gene in sporadic cerebral cavernomas", Neurology, vol. 60, pp. 1135-1138 (2003).*

Laberge et al.; "Familial Cavernous Angiomas CCM1 Gene Identification" *Eur. J. Hum. Gen.*; vol. 6; Suppl. 1; (1998) pp. 146.

Serebriiskii et al.; "Association of Krev-1/rap1a with Krit1, A Novel Ankyrin Repeat-containing Protein Encoded by a Gene Mapping to 7q21-22" *Oncogene*; vol. 15, (1997) pp. 1043-1049.

Laberge et al.; "Genetic Heterogeneity and Absence of Founder Effect in a Series of 36 French Cerebral Cavernous Angiomas Families" *Eur. J. Hum. Gen.*; vol. 7, (1999) pp. 499-504.

Craig et al.; Multilocus Linkage Identifies Two New loci for a Mendelian Form of Stroke, Cerebral Cavernous Malformation, at 7p-15-13 and 3q25.2-27; *Hum. Mol. Gen.*; vol. 7, No. 2, (1998) pp. 1851-1858.

Sahoo et al.; Mutations in the Gene Encoding KRIT1, a Krev-1/rap1a Binding Protein, Cause Cerebral Cavernous Malformations (CCM1); *Hum. Mol. Gen.*; vol. 8, No. 12, (1999) pp. 2325-2333.

Couteulx et al.; Truncating Mutations in *CCM1*, Encoding KRIT1, Cause Hereditary Cavernous Angiomas; *Nature Genetics*; vol. 23, No. 2, (1999) pp. 189-193.

* cited by examiner

*Primary Examiner*—Teresa E. Strzelecka
(74) *Attorney, Agent, or Firm*—Finnegan, Henderson, Farabow, Garrett & Dunner, LLP.

(57) ABSTRACT

The invention concerns a method for diagnosing cavernous angiomas for detecting mutations in the Krit1 gene. More particularly, said detection is performed by using nucleotide sequences. The invention further concerns the use of the Krit1 gene for therapeutic purposes in the field of angiogenesis.

12 Claims, 3 Drawing Sheets

SEQUENCE LISTING

```
<160> NUMBER OF SEQ ID NOS: 51

<210> SEQ ID NO 1
<211> LENGTH: 18
<212> TYPE: DNA
<213> ORGANISM: Artificial Sequence
<220> FEATURE:
<223> OTHER INFORMATION: Sense primer

<400> SEQUENCE: 1
gagcggataa aaactaat                                                  18

<210> SEQ ID NO 2
<211> LENGTH: 18
<212> TYPE: DNA
<213> ORGANISM: Artificial Sequence
<220> FEATURE:
```

-continued

```
<223> OTHER INFORMATION: Reverse primer

<400> SEQUENCE: 2
gagctaaaat tcattcaa                                                 18

<210> SEQ ID NO 3
<211> LENGTH: 18
<212> TYPE: DNA
<213> ORGANISM: Artificial Sequence
<220> FEATURE:
<223> OTHER INFORMATION: Sense primer

<400> SEQUENCE: 3
gctcttaatg ggttttg                                                  18

<210> SEQ ID NO 4
<211> LENGTH: 18
<212> TYPE: DNA
<213> ORGANISM: Artificial Sequence
<220> FEATURE:
<223> OTHER INFORMATION: Reverse primer

<400> SEQUENCE: 4
agcaatgtgg agtaaaac                                                 18

<210> SEQ ID NO 5
<211> LENGTH: 18
<212> TYPE: DNA
<213> ORGANISM: Artificial Sequence
<220> FEATURE:
<223> OTHER INFORMATION: Sense primer

<400> SEQUENCE: 5
tttggaatga gaacagtc                                                 18

<210> SEQ ID NO 6
<211> LENGTH: 18
<212> TYPE: DNA
<213> ORGANISM: Artificial Sequence
<220> FEATURE:
<223> OTHER INFORMATION: Reverse primer

<400> SEQUENCE: 6
gtcctgttgt atttttca                                                 18

<210> SEQ ID NO 7
<211> LENGTH: 18
<212> TYPE: DNA
<213> ORGANISM: Artificial Sequence
<220> FEATURE:
<223> OTHER INFORMATION: Sense primer

<400> SEQUENCE: 7
gttgttgttt tttgtttg                                                 18

<210> SEQ ID NO 8
<211> LENGTH: 18
<212> TYPE: DNA
<213> ORGANISM: Artificial Sequence
<220> FEATURE:
<223> OTHER INFORMATION: Reverse primer

<400> SEQUENCE: 8
acctggaaaa taacttac                                                 18
```

```
<210> SEQ ID NO 9
<211> LENGTH: 18
<212> TYPE: DNA
<213> ORGANISM: Artificial Sequence
<220> FEATURE:
<223> OTHER INFORMATION: Sense primer

<400> SEQUENCE: 9
atgtaatgcc ttttttcc                                                    18

<210> SEQ ID NO 10
<211> LENGTH: 18
<212> TYPE: DNA
<213> ORGANISM: Artificial Sequence
<220> FEATURE:
<223> OTHER INFORMATION: Reverse primer

<400> SEQUENCE: 10
atgcctggct ctaactat                                                    18

<210> SEQ ID NO 11
<211> LENGTH: 18
<212> TYPE: DNA
<213> ORGANISM: Artificial Sequence
<220> FEATURE:
<223> OTHER INFORMATION: Sense primer

<400> SEQUENCE: 11
ttgttagatt gtgatgta                                                    18

<210> SEQ ID NO 12
<211> LENGTH: 18
<212> TYPE: DNA
<213> ORGANISM: Artificial Sequence
<220> FEATURE:
<223> OTHER INFORMATION: Reverse primer

<400> SEQUENCE: 12
aacataataa aaactttc                                                    18

<210> SEQ ID NO 13
<211> LENGTH: 18
<212> TYPE: DNA
<213> ORGANISM: Artificial Sequence
<220> FEATURE:
<223> OTHER INFORMATION: Sense primer

<400> SEQUENCE: 13
tttataaaag gaatgatg                                                    18

<210> SEQ ID NO 14
<211> LENGTH: 18
<212> TYPE: DNA
<213> ORGANISM: Artificial Sequence
<220> FEATURE:
<223> OTHER INFORMATION: Reverse primer

<400> SEQUENCE: 14
tcaactcaaa ccatatca                                                    18

<210> SEQ ID NO 15
<211> LENGTH: 18
<212> TYPE: DNA
<213> ORGANISM: Artificial Sequence
<220> FEATURE:
<223> OTHER INFORMATION: Sense primer
```

```
<400> SEQUENCE: 15
tgtagcctaa taaccaaa                                              18

<210> SEQ ID NO 16
<211> LENGTH: 18
<212> TYPE: DNA
<213> ORGANISM: Artificial Sequence
<220> FEATURE:
<223> OTHER INFORMATION: Reverse primer

<400> SEQUENCE: 16
agcatagcac aagaccat                                              18

<210> SEQ ID NO 17
<211> LENGTH: 18
<212> TYPE: DNA
<213> ORGANISM: Artificial Sequence
<220> FEATURE:
<223> OTHER INFORMATION: Sense primer

<400> SEQUENCE: 17
ggtgaagttt ttaatatg                                              18

<210> SEQ ID NO 18
<211> LENGTH: 18
<212> TYPE: DNA
<213> ORGANISM: Artificial Sequence
<220> FEATURE:
<223> OTHER INFORMATION: Reverse primer

<400> SEQUENCE: 18
caatagttta tgaagtcc                                              18

<210> SEQ ID NO 19
<211> LENGTH: 18
<212> TYPE: DNA
<213> ORGANISM: Artificial Sequence
<220> FEATURE:
<223> OTHER INFORMATION: Sense primer

<400> SEQUENCE: 19
atatttacaa aggcaagc                                              18

<210> SEQ ID NO 20
<211> LENGTH: 18
<212> TYPE: DNA
<213> ORGANISM: Artificial Sequence
<220> FEATURE:
<223> OTHER INFORMATION: Reverse primer

<400> SEQUENCE: 20
tgacatgatt ggtaaaaa                                              18

<210> SEQ ID NO 21
<211> LENGTH: 18
<212> TYPE: DNA
<213> ORGANISM: Artificial Sequence
<220> FEATURE:
<223> OTHER INFORMATION: Sense primer

<400> SEQUENCE: 21
tggtacattt tcctttca                                              18

<210> SEQ ID NO 22
<211> LENGTH: 18
```

```
<212> TYPE: DNA
<213> ORGANISM: Artificial Sequence
<220> FEATURE:
<223> OTHER INFORMATION: Reverse primer

<400> SEQUENCE: 22
ctttatgatt gctggggc                                                  18

<210> SEQ ID NO 23
<211> LENGTH: 18
<212> TYPE: DNA
<213> ORGANISM: Artificial Sequence
<220> FEATURE:
<223> OTHER INFORMATION: Sense primer

<400> SEQUENCE: 23
ggtgaagttt ttaatatg                                                  18

<210> SEQ ID NO 24
<211> LENGTH: 18
<212> TYPE: DNA
<213> ORGANISM: Artificial Sequence
<220> FEATURE:
<223> OTHER INFORMATION: Reverse primer

<400> SEQUENCE: 24
caatagttta tgaagtcc                                                  18

<210> SEQ ID NO 25
<211> LENGTH: 18
<212> TYPE: DNA
<213> ORGANISM: Artificial Sequence
<220> FEATURE:
<223> OTHER INFORMATION: Sense primer

<400> SEQUENCE: 25
aatagatagg gaactgcc                                                  18

<210> SEQ ID NO 26
<211> LENGTH: 18
<212> TYPE: DNA
<213> ORGANISM: Artificial Sequence
<220> FEATURE:
<223> OTHER INFORMATION: Reverse primer

<400> SEQUENCE: 26
gtggcttgag taacagtt                                                  18

<210> SEQ ID NO 27
<211> LENGTH: 18
<212> TYPE: DNA
<213> ORGANISM: Artificial Sequence
<220> FEATURE:
<223> OTHER INFORMATION: Sense primer

<400> SEQUENCE: 27
taatgcccac tgaaagaa                                                  18

<210> SEQ ID NO 28
<211> LENGTH: 18
<212> TYPE: DNA
<213> ORGANISM: Artificial Sequence
<220> FEATURE:
<223> OTHER INFORMATION: Reverse primer

<400> SEQUENCE: 28
```

| | |
|---|---|
| ggctggtctt gaactctg | 18 |

<210> SEQ ID NO 29
<211> LENGTH: 20
<212> TYPE: DNA
<213> ORGANISM: Homo sapiens

<400> SEQUENCE: 29

| | |
|---|---|
| atcaggtcag acagaaaact | 20 |

<210> SEQ ID NO 30
<211> LENGTH: 20
<212> TYPE: DNA
<213> ORGANISM: Homo sapiens

<400> SEQUENCE: 30

| | |
|---|---|
| tacaaatcgg gtaagagttg | 20 |

<210> SEQ ID NO 31
<211> LENGTH: 20
<212> TYPE: DNA
<213> ORGANISM: Homo sapiens

<400> SEQUENCE: 31

| | |
|---|---|
| ccctttctag gtagataaag | 20 |

<210> SEQ ID NO 32
<211> LENGTH: 20
<212> TYPE: DNA
<213> ORGANISM: Homo sapiens

<400> SEQUENCE: 32

| | |
|---|---|
| cagaagacaa gtactgtttc | 20 |

<210> SEQ ID NO 33
<211> LENGTH: 20
<212> TYPE: DNA
<213> ORGANISM: Homo sapiens

<400> SEQUENCE: 33

| | |
|---|---|
| taatgattag ggaacgacag | 20 |

<210> SEQ ID NO 34
<211> LENGTH: 20
<212> TYPE: DNA
<213> ORGANISM: Homo sapiens

<400> SEQUENCE: 34

| | |
|---|---|
| atgcatgctg gtaaatggaa | 20 |

<210> SEQ ID NO 35
<211> LENGTH: 20
<212> TYPE: DNA
<213> ORGANISM: Homo sapiens

<400> SEQUENCE: 35

| | |
|---|---|
| ttttatacag gtatggaaaa | 20 |

<210> SEQ ID NO 36
<211> LENGTH: 20
<212> TYPE: DNA
<213> ORGANISM: Homo sapiens

<400> SEQUENCE: 36

-continued

```
aacggataga gtaagttatt                                              20

<210> SEQ ID NO 37
<211> LENGTH: 20
<212> TYPE: DNA
<213> ORGANISM: Homo sapiens

<400> SEQUENCE: 37
acatttctag catataacag                                              20

<210> SEQ ID NO 38
<211> LENGTH: 20
<212> TYPE: DNA
<213> ORGANISM: Homo sapiens

<400> SEQUENCE: 38
taacaaacca gtaagaatta                                              20

<210> SEQ ID NO 39
<211> LENGTH: 20
<212> TYPE: DNA
<213> ORGANISM: Homo sapiens

<400> SEQUENCE: 39
tttcttgtag tatgaaaaag                                              20

<210> SEQ ID NO 40
<211> LENGTH: 20
<212> TYPE: DNA
<213> ORGANISM: Homo sapiens

<400> SEQUENCE: 40
gaaaacctca gtaagaaagt                                              20

<210> SEQ ID NO 41
<211> LENGTH: 20
<212> TYPE: DNA
<213> ORGANISM: Homo sapiens

<400> SEQUENCE: 41 tgttttcag gccttcaact                                               20

<210> SEQ ID NO 42
<211> LENGTH: 20
<212> TYPE: DNA
<213> ORGANISM: Homo sapiens

<400> SEQUENCE: 42
tgaaaaacag gtttgcttgg                                              20

<210> SEQ ID NO 43
<211> LENGTH: 20
<212> TYPE: DNA
<213> ORGANISM: Homo sapiens

<400> SEQUENCE: 43
ttcctttaag attgaagacc                                              20

<210> SEQ ID NO 44
<211> LENGTH: 20
<212> TYPE: DNA
<213> ORGANISM: Homo sapiens
```

-continued

```
<400> SEQUENCE: 44
gtttcctaaa gtaagtattt                                              20

<210> SEQ ID NO 45
<211> LENGTH: 20
<212> TYPE: DNA
<213> ORGANISM: Homo sapiens

<400> SEQUENCE: 45
gtgcttacag tgaagaaaat                                              20

<210> SEQ ID NO 46
<211> LENGTH: 20
<212> TYPE: DNA
<213> ORGANISM: Homo sapiens

<400> SEQUENCE: 46
tgaatacaag gtaagctgtt                                              20

<210> SEQ ID NO 47
<211> LENGTH: 20
<212> TYPE: DNA
<213> ORGANISM: Homo sapiens

<400> SEQUENCE: 47 ttgttttag aatctcagta                                               20

<210> SEQ ID NO 48
<211> LENGTH: 20
<212> TYPE: DNA
<213> ORGANISM: Homo sapiens

<400> SEQUENCE: 48
ggaaactaag gtagattttc                                              20

<210> SEQ ID NO 49
<211> LENGTH: 20
<212> TYPE: DNA
<213> ORGANISM: Homo sapiens

<400> SEQUENCE: 49
tatgttgcag gctttactca                                              20

<210> SEQ ID NO 50
<211> LENGTH: 20
<212> TYPE: DNA
<213> ORGANISM: Homo sapiens

<400> SEQUENCE: 50
tacaaaacag gtaagtatca                                              20

<210> SEQ ID NO 51
<211> LENGTH: 20
<212> TYPE: DNA
<213> ORGANISM: Homo sapiens

<400> SEQUENCE: 51
tactttgtag gctctggtcg                                              20
```

USE OF THE *KRIT1* GENE IN THE FIELD OF ANGIOGENESIS

Figure 1:
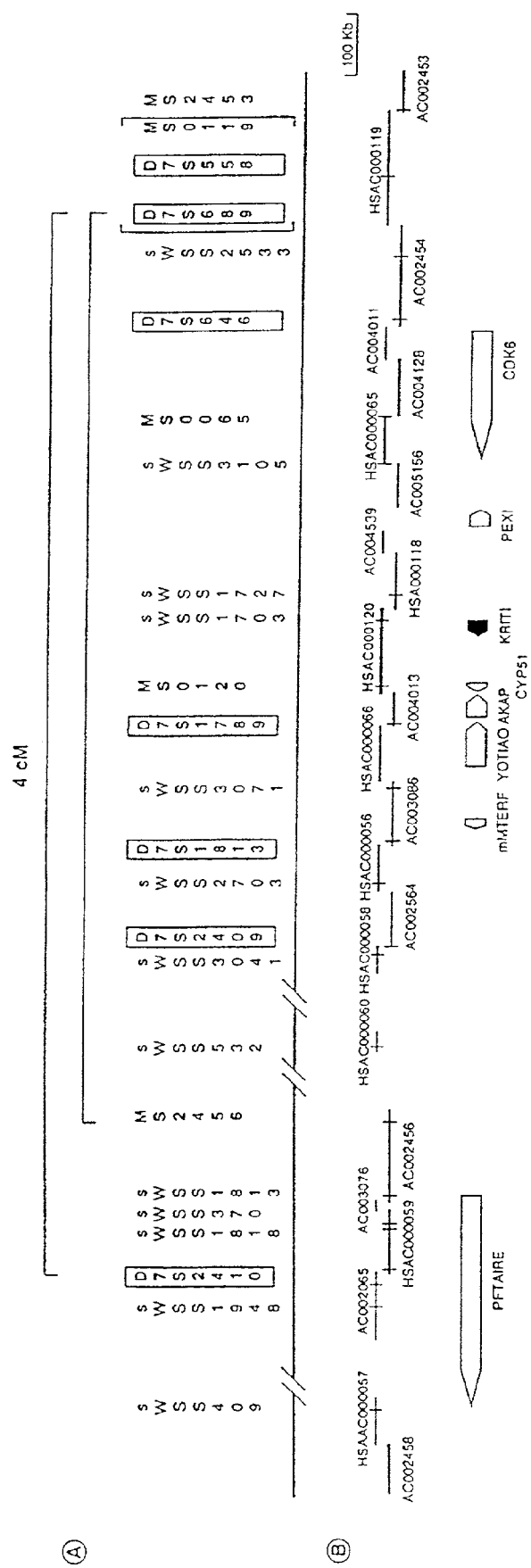

The present invention relates to a method for diagnosing cavernous angiomas, or cavernomas, for the detection of mutations in the Krit1 gene. In particular, this detection is carried out using nucleotide sequences which are also the subject of the present invention. The invention also relates to the use of all or part of the Krit1 gene for therapeutic purposes in the field of pro- or anti-angiogenesis.

Cavernomas are vascular malformations most commonly located in the central nervous system, but also in the retina, the liver, the kidneys, etc., and are characterized by capillary cavities which are abnormally enlarged without involvement of cerebral parenchyma (Russell et al.). The clinical symptoms comprise headaches, hemorrhages, epileptic fits and focal neurological deficiencies. The prevalence of cavernous angiomas is close to 0.5% in the general population (Otten et al.). These angiomas may be transmitted in a hereditary manner, in an autosomal dominant form, in close to 50% of cases (Rigamonti et al.). 3 locations (or loci) for cerebral cavernous malformations (CCMs) have been identified on the long arm of chromosome 7, the short arm of chromosome 7 and the long arm of chromosome 3 (7q, 7p and 3q, respectively). A considerable founder effect has been observed in the Hispano-American population, in which all the families are linked to the CCM1 locus located on 7q (Rigamonti et al.; Dubovsky et al.; Günel et al.; and Craig et al.).

The inventors have recently established the genetic and clinical characteristics of cavernomas, and also the hereditary characteristics in a series of 57 French families (Labauge et al.). Neuroimaging investigations have confirmed the high frequency of multiple lesions in hereditary cavernomas. A highly significant correlation has also been demonstrated between the number of lesions and the age of the patient, which strongly suggests the dynamic nature of these vascular malformations, also termed hamartomas. The genetic linkage analysis carried out in 36 of these families has shown that 65% of them are linked to the CCM1 locus, with no founder effect (Laberge et al.).

The size of the genetic interval containing the CCM1 locus had, in 1995, been reduced to 4 centimorgans, the CCM1 locus being flanked by D7S2410 and D7S689 (Johnson et al.). Using essentially an in silico approach, the inventors established a physical and transcriptional map of the CCM1 interval. Among the 53 transcriptional units mapped within the essential region, one of them corresponded to Krit1, a gene the product of which interacts with Rap1A (also termed Krev1), a member of the family of Ras genes involved in cell proliferation, differentiation and morphogenesis (Bos et al.). Using the SSCP technique and sequencing in combination, the inventors identified, in 8 unrelated CCM1 families, mutations which very probably lead to a truncated Krit1 protein. The cosegregation of these mutations with the affected phenotype strongly suggests that Krit1 is the protein mutated in the families suffering from cavernomas linked to the CCM1 locus, and suggests that the Rap1A signal transduction pathway is involved in vasculogenesis and/or angiogenesis.

Using a previously published YAC contig and public sequence databases (The Washington University Chromosome 7 Project), the inventors constructed BAC/PAC contigs covering 90% of the CCM1 interval, estimated at 1 600 Kb (FIG. 1). 20 families comprising 179 potentially informative meioses, for which it had previously been shown that they had a probability, a posteriori, of being linked to the CCM1 locus of greater than 90%, were used to finely map this locus with polymorphic markers identified using the BAC/PAC sequences (FIG. 1). A recombination event observed in an affected individual (family 27 in Labauge et al.) allowed the inventors to slightly reduce this interval, which is now flanked by M2456 (centromeric limit) and D7S689 (telomeric limit). The screening of public databanks, such as Gene Map of the Human Genome, Unigene and dBEST, allowed the inventors to map, within this interval, 574 Expressed Sequence Tags (ESTS), which were then regrouped into 53 putative transcriptional units comprising 6 already known genes: CDK6, HUMI.D14, KRIT1, PEX-1. mMTERF and Yotiao.

Krit1 had been identified during a screening intended to identify the proteins which interact with Rap1A/Krev1, a member of the Ras gene family (Serebriiski et al.). It encodes a 529 amino acid protein which comprises 4 ankyrin domains and interacts with Rap1A/Krev1 by means of its carboxyterminal region. It had already been indicated that the Krit1 messenger RNA was expressed at low levels in many tissues, including the brain. Although the exact function of Krit1 is still unknown, the inventors considered that it was a good candidate gene for CCM1, this being for several reasons. Rap1A/Krev1A was identified on the basis of its homology with Dras3, a Ras homologue in *drosophila*, and also on the basis of its antimitogenic activity in fibroblasts transformed with K-ras (Pizon et al., 1988/Kitayama et al., 1989). Although the physiological relevance of this anti-mitogenic effect observed in vitro has not yet been established in vivo, this has led to this protein being considered a Ras antagonist. A role for the Ras signaling pathway in vasculogenesis and angiogenesis has been strongly suggested by the vascular abnormalities observed in the murine models which are knock-outs for the proteins involved in this pathway, for example the raf or GAP120 proteins (Henkemeyer et al., 1995; Wojnowski et al., 1997). In addition to this putative role as an Ras antagonist, Rap1A/Krev1 has been implicated in cellular differentiation and morphogenesis (Asha et al., 1999; Quarck et al., 1996; Pizon et al., 1988).

In other words, insofar as the trunctated Krit1 protein gives rise to an abnormality of angiogenesis accompanied by endothelial cell proliferation, it is reasonable to deduce therefrom that the Krit1 gene may have a role in controlling angiogenesis.

Thus, in the context of the present invention, the inventors have shown that mutations in the Krit1 gene, capable of giving rise to a truncated Krit1 protein, are responsible for the appearance of vascular abnormalities. These vascular abnormalities may affect various areas, including the brain and the skin, and take various forms (cavernomas, capillary-venous angiomas). The type of the lesions observed (development of abnormal vascular diseases) combined with the nature of the mutations observed (mutations leading to truncation of the protein) strongly suggest that this protein exerts a control over angiogenesis, which it may be possible to use therapeutically in the field of anti-angiogeneis, in particular in the tumor field.

The alignment of the Krit1 cDNA with the BAC AC000020, one of the BACs located in the interval, has allowed the inventors to determine the genomic structure of Krit1. This gene is encoded by 12 exons, which are all included in the BAC AC000020. The inventors have illustrated the intronic oligonucleotide primers intended to amplify the exons (Table No. 1) and also the junction sequences (Table No. 2). These primers were particularly tricky to develop because Krit1 is rich in A and T bases, and are very specific for Krit1. Thus, a subject of the present invention is a nucleotide sequence chosen from the group comprising SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 and SEQ ID No. 28.

By means of these primers, the inventors have been able to amplify all the exons. A set of 20 unrelated CCM patients belonging to families in which the HOMOG analysis showed a probability, a posteriori, of being linked to the CCM1 locus of greater than 90%, has made it possible to screen mutations using an analysis which combines an approach of the Single Strand Conformation Polymorphism (SSCP) type, under 4 distinct conditions, and a sequencing approach.

The amplified products of 8 of these patients showed abnormal conformational variants which were not observed in any of the 50 control individuals. Analysis of the sequence of these amplimers revealed heterozygous mutations in these 8 patients (Table 3 and FIG. 3). These mutations cosegregated with the diseased phenotype in the 8 families of these patients.

A subject of the present invention is also the use of at least one nucleotide sequence as defined above for detecting, from a biological sample, the presence of a mutation in the Krit1 gene, preferably a mutation linked to the occurrence of vascular abnormalities as defined above. Preferentially, the biological sample is blood.

More particularly, pedigree 6 exhibits deletion of an A at nucleotide 1342, in exon 10. This deletion leads to a change in the reading frame and thus to a premature stop codon. In pedigree 10, substitution of C with T at nucleotide 1283 in exon 10 leads to the replacement of a glutamine with a stop codon. Pedigree 58, itself, shows insertion of a C after nucleotide 1271, also in exon 10, which leads to a change in the reading frame and a premature stop codon. Pedigree 41 shows substitution of G with A at nucleotide 615, which leads to the replacement of a tryptophan with a premature stop codon in exon 5. Pedigree 42 exhibits a 4 bp deletion (nucleotides 681-684) in exon 6, which gives rise to a premature stop codon. Pedigree 35 exhibits a 26 bp deletion (nucleotides 1012-1037) in exon 8, this deletion causing a change in the reading frame and a premature stop codon at codon 332. Pedigree 18 exhibits insertion of a C in exon 2 after nucleotide 247, this insertion leading to a change in the reading frame and a premature stop codon. Pedigree 19 shows substitution of a G with an A at nucleotide 261, this substitution causing a change in the reading frame and also a premature stop codon at codon 79.

Figure 3:
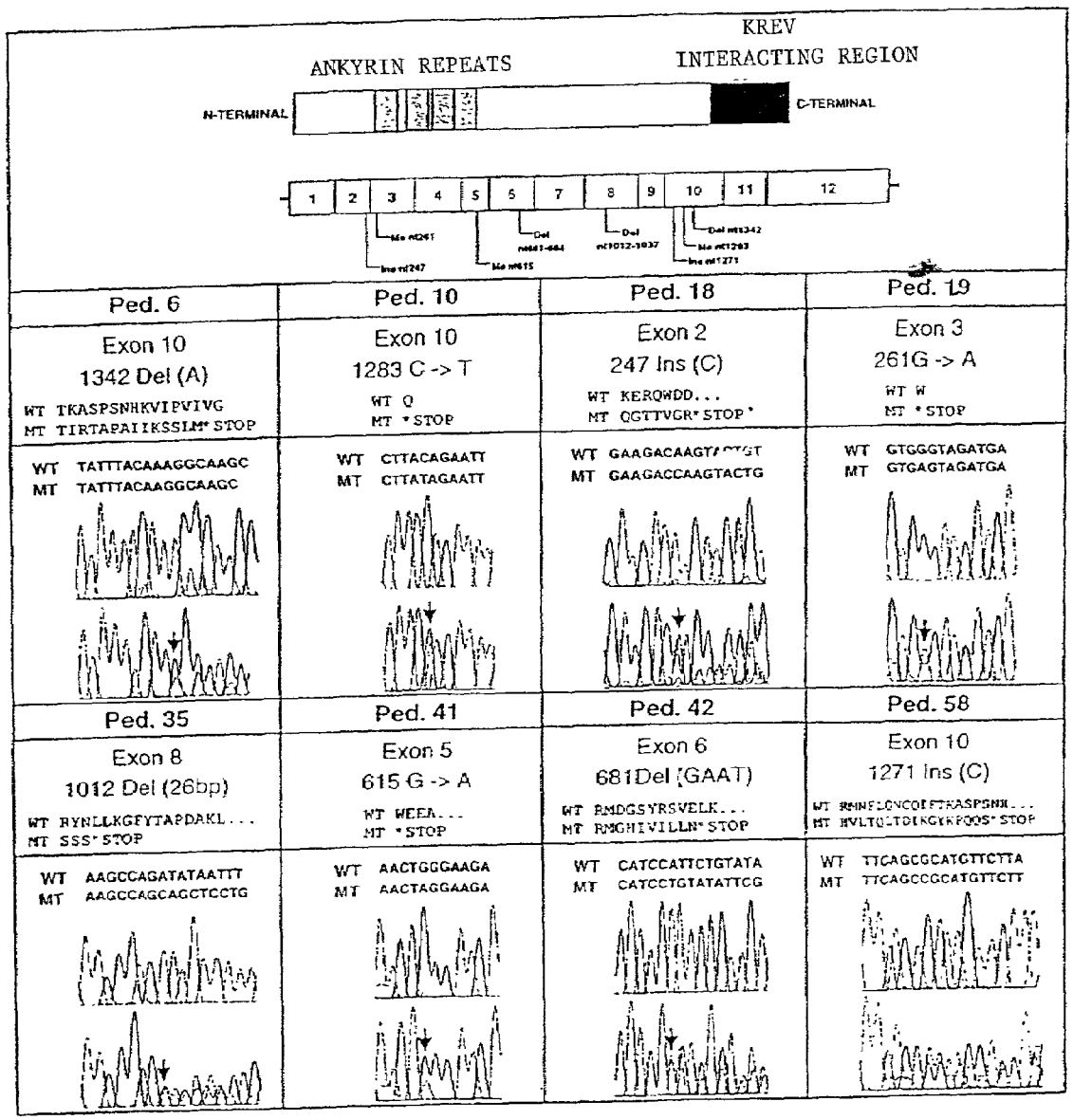

The SSCP analyses of the affected and unaffected members have shown perfect cosegretation of the mutations with the affected phenotype in each of these 8 pedigrees (FIG. 3).

Thus, the nucleotide sequences in accordance with the present invention are used to detect a mutation in at least one exon of the Krit1 gene. More particularly, these nucleotide sequences may be used in pairs, given their specificity for an exon, according to the following distribution:

SEQ ID No. 1/SEQ ID No. 2 for exon 1,
SEQ ID No. 3/SEQ ID No. 4 for exon 2,
SEQ ID No. 5/SEQ ID No. 6 for exon 3,
SEQ ID No. 7/SEQ ID No. 8 for exon 4,
SEQ ID No. 9/SEQ ID No. 10 for exon 5,
SEQ ID No. 1/SEQ ID No. 12 for exon 6,
SEQ ID No. 13/SEQ ID No. 14 for exon 7,
SEQ ID No. 15/SEQ ID No. 16 for exon 8,
SEQ ID No. 17/SEQ ID No. 18 for exon 9,
SEQ ID No. 19/SEQ ID No. 20 for exon 10,
SEQ ID No. 21/SEQ ID No. 22 for exon 10,
SEQ ID No. 23/SEQ ID No. 24 for exon 11,
SEQ ID No. 25/SEQ ID No. 26 for exon 12,
SEQ ID No. 27/SEQ ID No. 28 for exon 12.

Advantageously, the detection of a mutation in Krit1 is preceded by amplification of the exon in which the mutation is being sought, and this amplification may be carried out by PCR or PCR-like amplification.

The truncating nature of these mutations, their absence in the healthy controls and their consegregation with the affected phenotype strongly suggest that they are mutations which are deleterious in these families.

The inventors did not detect any abnormal SSCP conformational variants in 12 of the 20 families tested. Several hypotheses may be put forward to explain this. SSCP is not 100% sensitive, even when several types of condition are used, as was the case here. Interestingly, none of these abnormal conformational variants was observed in the first screening, which was carried out at 20° C. without glycerol. In addition, it would not have been possible to detect, using this approach, the deletions which would take away the regions containing the sequences which hybridize with the primers. Finally, some of these families, although showing a high probability of being linked to the CCM1 locus, may, in fact, be linked to one of the other CCM loci.

A subject of the present invention is also a method for genotypically diagnosing vascular abnormalities in an individual, comprising taking a biological sample from said individual, and also detecting the presence of a mutation in the Krit1 gene by analyzing the sequence of nucleic acids present in said sample, such a mutation being linked to the occurrence of vascular abnormalities. The nucleic acid sequence analyzed may be, indifferently, genomic DNA, cDNA or mRNA. The analysis may be carried out by hybridization, by sequencing or by electrophoretic migration, in particular by SSCP or DGGE (denaturing gradient gel electrophoresis). The detection of these mutations may also be carried out using methodology which makes it possible to directly detect the presence of the truncated protein, for example the "Protein Truncation Test" methods (in vitro translation of cDNA reverse transcripts, followed by revelation of the protein with antibodies or after labeling the protein using a labeled amino acid). Finally, the search for mutations may be carried out by direct analysis of the cDNA reverse transcript prepared from total RNAs (in particular originating from cells transformed with the EBV virus, cells in which the authors have shown the expression of the Krit1 transcript).

Advantageously, all or part of the nucleic acid sequence corresponding to the Krit1 gene is amplified prior to detecting the presence of a mutation, this amplification possibly being carried out by PCR or PCR-like amplification. Entirely preferentially, this amplification may be carried out using primers chosen from the nucleic acid sequences in accordance with the present invention, for example used according to the abovementioned distribution.

The main question is therefore to understand how these mutations were able to lead to cavernomas. Little is, in reality, known about the nature of these lesions, which are considered to be vascular malformations or hamartomas. It would appear that the period when these malformations appear during embryonic life is not entirely clear. In addition, in certain cases, particularly in familial cases, progressive extension of these hamartomas has been described: it has been suggested that these lesions may express factors and/or receptors involved in angiogenesis (Rothbart et al., 1996; Notelet et al., 1997).

It should be pointed out that the inventors have observed, in four families (Labauge et al., 1999) that cutaneous malformations (also termed angiomas) may segregate with cerebral cavernomas.

All the mutations reported herein would, if they were translated, produce truncated Krit1 proteins which would be deleted of the region which interacts with Rap1A/Krev1.

The exact functions of Rap1A/Krev1 have not been entirely elucidated. This member of the Ras GTPase family is expressed ubiquitously, particularly in neutrophils, platelets and the brain; it is located in the endocytic/lysosomal compartments. Rap1A has been described as interacting with B-Raf, which is quite interesting given the massive endothelial apoptosis observed in mice deficient in B-Raf (Wojnowski et al., 1997). In vivo, studies on lower eukaryotes, such as yeasts and *drosophila*, have recently given some indications concerning the functions of Rap1A in differentiation and morphogenesis (Asha et al.).

The interaction of Krit1 and Rap1A suggests that Krit1 may either regulate Rap1A or be an effector of Rap1A (Bos et al.). The mutations reported herein may result either from a dominant negative effect or from a loss of function. The observation of families exhibiting complete deletions of Krit1 would be a strong argument in favor of this hypothesis. Moreover, the fact that the sporadic forms of cavernomas manifest themselves mainly as a single lesion, and that the familial forms manifest themselves not multiple lesions, strongly suggests that these lesions follow the "Knudson double hit" rule (Knudson 1971) and that a complete loss of Krit1 function may be necessary for the appearance of cavernomas.

In other words, in the dominant forms of the disease, a first mutation, present in all the cells of the organism in the heterozygous state, would be present. The appearance of the cavernomatous lesions would be conditioned by the occurrence of a second mutation affecting the other allele of this gene, this mutation occurring somatically. In the sporadic forms most studied to date, the individual exhibits no germinal mutation and the single lesion is thought to result from two mutations which have occurred in the same cell.

However, sporadic forms of cavernomas other than those described above are thought to exist. The inventors have, in fact, demonstrated a sporadic form which manifests itself as multiple lesions and results from a de novo mutation in the Krit1 gene, probably in a germinal cell of one of the two parents of the patient affected (data not shown).

In summary, the data reported herein strongly suggest that the truncating mutations of Krit1 are responsible for the appearance of the cerebral cavernomas observed in the CCM1 families, but also in certain sporadic forms, underlining the putative role of the Rap1A signaling pathway in these mechanisms.

Among the therapeutic applications with which the present invention is concerned, there may be various types of vascular malformations, vascular dysplasias, angiomas and/or any situation in which abnormal angiogenesis exists.

Thus, a subject of the present invention is also the use of the Krit1 gene, or of a sequence derived from this gene, for producing a medicinal product, or its use in an approach of the gene therapy type intended to control or inhibit angiogenesis, in particular by over-expression, in situ, of the Krit1 gene or a sequence derived from this gene.

The expression "sequence derived from this gene" is intended to mean any normal or mutated sequence, or portion of sequence, of the Krit1 gene, which exhibits an activity similar and comparable to the total functional reference sequence.

A subject of the present invention is also a vector for expression in a suitable host cell, comprising the sequence of the Krit1 gene or a sequence derived from this gene (the derived sequence is defined above). When the intention would be to repress abnormal angiogenesis, it may be advantageous to overexpress the sequence in question and, for this reason, the vector in accordance with the invention advantageously comprises the elements required for this overexpression.

In particular, the vector in accordance with the invention may be intended for gene therapy and, when the intention would be to limit its site of action, this vector may comprise a sequence for the tissue-specific targeting and/or expression of the sequences which it comprises.

Finally, the subject of the present invention is a therapeutic composition comprising, as active principle, all or part of the normal or modified Krit1 protein, so as to substitute, for example, for a truncated protein and compensate for the deficiency. The active principle may also be a vector as described above.

FIG. 1 represents the genetic, physical and transcriptional map of the CCM1 locus.

FIG. 1*a* represents the genetic map of the CCM1 locus. This locus was previously defined by the D7S2410-D7S689 interval. The reduced MS2456-D7S689 genetic intervals are indicated by horizontal square brackets. The micro-satellites already published are boxed. The new micro-satellites are identified by bold characters. Some of the STSs are also shown. The STS sWSS 1703 corresponds to nucleotides 393-658 of Krit1. The markers between the vertical square brackets are less than 1 kb apart.

FIG. 1*b* represents the physical and transcriptional map of the CCM1 locus. BAC contigs are distributed over the CCM1 interval. The BAC AC000120 is represented by the thickest line. The overlaps with either the STSs or the microsatellite markers are indicated by small vertical bars. The black arrow corresponds to Krit1, the white arrows correspond to well-characterized human genes and the empty arrows correspond to genes exhibiting strong homologies with genes from other species (not characterized in humans).

Figure 2:
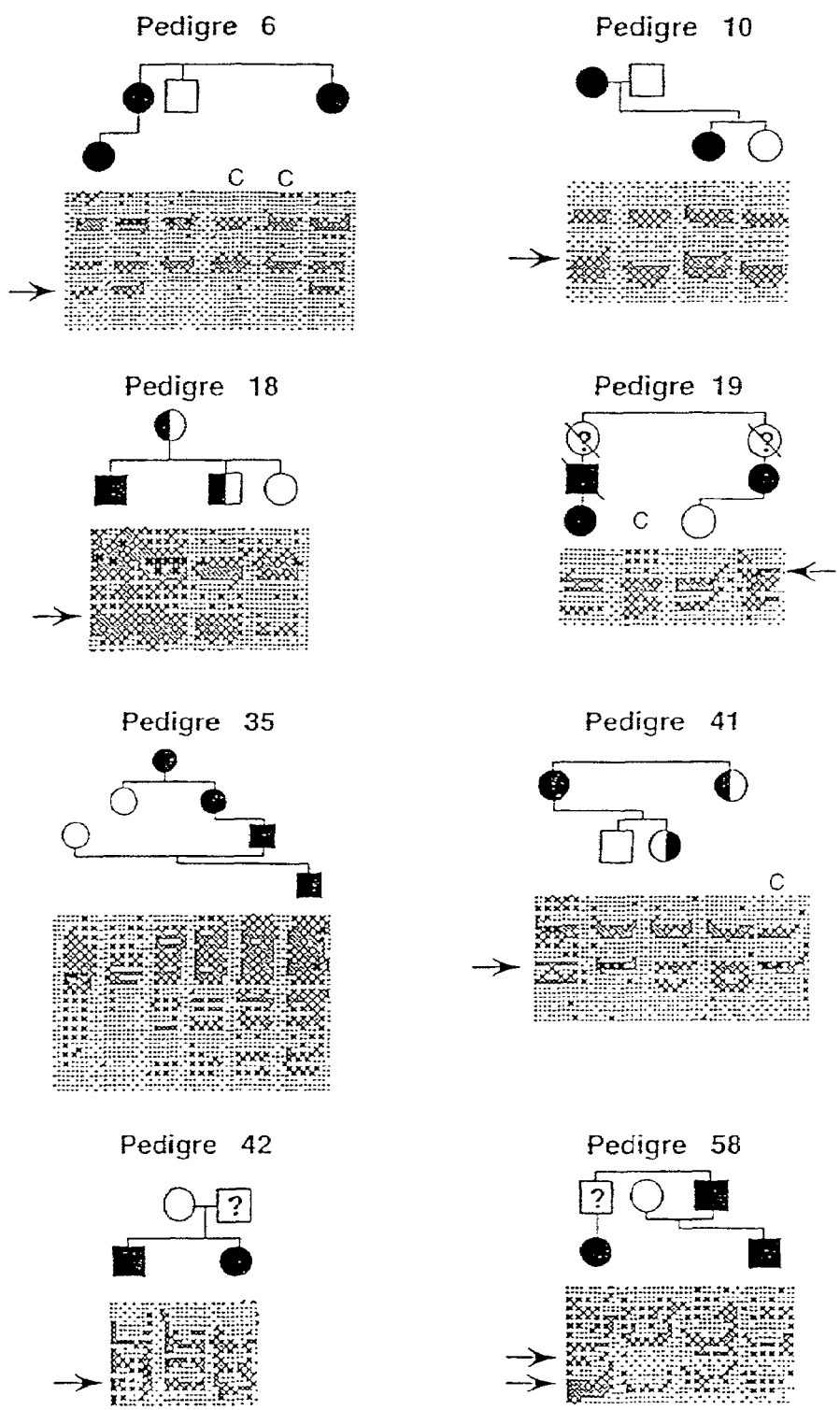

FIG. 2 represents the cosegregation of the conformational variants with the disease phenotype, within 8 pedigrees (SSCP).

The empty symbols denote the individuals whose MRI examination of the brain is normal, the half-full black symbols correspond to asymptomatic patients exhibiting cavernomas on the MRI examination, and the full black symbols correspond to symptomatic patients exhibiting cavernomas on the MRI; the sign "?" corresponds to the individuals having an unknown status, and the sign "\" corresponds to deceased patients. The deceased patients or patients with unknown status were not tested for the mutation but are represented in the interests of clear understanding of the familial structures. The abnormal bands are indicated with an arrow.

FIG. 3 illustrates the Krit1 mutations.

FIG. 3*a* represents the structure of the Krit1 gene and of the corresponding putative protein. "ns" signifies nonsense, "del" signifies deletion, and "ins" signifies insertion. For the insertions, the nucleotide number corresponds to the nucleotide preceding the insertion. The expression "Krev Interacting Region" corresponds to the region (amino acids 483-529) for which the deletion destroys the interaction with Krev during the double hybrid test in yeast.

FIG. 3b represents the Krit1 mutations identified in the 8 pedigrees mentioned above. The arrows indicate the mutation sites. WT signifies wild-type sequence, and MT signifies mutant sequence. In pedigree 42, the chromatogram and the sequence presented correspond to the negative strand; the positive strand showed complete superposition of the normal and abnormal sequences and did not allow good visualization of the start site of the deletion.

EXAMPLES

Materials and Methods

Patients 20 unrelated patients belonging to families who were known to exhibit cavernomas in a hereditary manner freely consented to take part in the study (Labauge et al.).

Analysis of this panel of families with the HOMOG test showed that these families had a probability, a posteriori, of being linked to the CCM1 locus of greater than 90% (Laberge et al.).

An approach combining molecular biology and bioinformatics was used to establish the physical and transcriptional map of the CCM1 locus. After validation of a contig of YACs previously published by Johnson et al. (1995), the authors positioned in the interval, by PCR and using an in silico approach, 574 EST (Expressed Sequence Tags) which they grouped into 53 groups.

Reduction of the genetic interval 12 polymorphic microsatellite markers covering the D7S2410-D7S689 interval were selected for the linkage analyses. 7 of them were previously known: D7S2410, D7S2409, D7S1813, D7S1789, D7S646, D7S689 and D7S558, and were used by several teams (Günel et al. in Neurosurgery, Craig et al., Labauge et al., Laberge et al.). The last ones, MS65, MS2453A, MS2456A, MS119 and MS120, were identified by the inventors on the basis of the sequence database for the BACs mapped in the interval.

Detection of Mutations and Identification

On the basis of the comparison of the sequences of the Krit1 cDNA and of the BAC AC 00000120, the inventors determined 14 sets of primers in order to amplify the 12 exons and the exon/intron junction sites of Krit1 using genomic DNA. PCR reactions were carried out as follows: after a first initial denaturation step at 94° C. (4 min), 30 amplification cycles consisting of steps at 94° C. (15 s), an optimized hybridization temperature of between 45° C. and 55° C. (15 s) and 72° C. (15 s), followed by a final extension step at 72° C. (10 min). The PCR products were subjected to electrophoresis under 4 types of condition (10% acrylamide with or without glycerol at 4° C. and 20° C.) on a Mighty Small II apparatus (Pharmacia-Biogen) used under conditions of constant current of 35 mA. Conformational variants were revealed with silver (Silver Stain Plus kit, Biorad). Amplimers showing an atypical SSCP band pattern were sequenced (AB1377, Perkin Elmer). All the mutations detected during the sequencing were tested for their cosegregation with the diseased phenotype, using an SSCP approach.

TABLE 1

PRIMERS

| EXON | SENSE PRIMER | REVERSE PRIMER | AMPLIMER SIZE |
|---|---|---|---|
| 1 | GAGCGGATAAAAACTAAT (SEQ ID No. 1) | GAGCTAAAATTCATTCAA (SEQ ID No. 2) | 205 |
| 2 | GCTCTTAATGGGTTTTTG (SEQ ID No. 3) | AGCAATGTGGAGTAAAAC (SEQ ID No. 4) | 183 |
| 3 | TTTGGAATGAGAACAGTC (SEQ ID No. 5) | GTCCTGTTGTATTTTTCA (SEQ ID No. 6) | 265 |
| 4 | GTTGTTGTTTTTTGTTTG (SEQ ID No. 7) | ACCTGGAAAATAACTTAC (SEQ ID No. 8) | 208 |
| 5 | ATGTAATGCCTTTTTTCC (SEQ ID No. 9) | ATGCCTGGCTCTAACTAT (SEQ ID No. 10) | 181 |
| 6 | TTGTTAGATTGTCATGTA (SEQ ID No. 11) | AACATAATAAAAACTTTC (SEQ ID No. 12) | 257 |
| 7 | TTTATAAAAGGAATGATG (SEQ ID No. 13) | TCAACTCAAACCATATCA (SEQ ID No. 14) | 335 |
| 8 | TGTAGCCTAATAACCAAA (SEQ ID No. 15) | AGCATAGCACAAGACCAT (SEQ ID No. 16) | 243 |
| 9 | GGTGAAGTTTTTAATATG (SEQ ID No. 17) | CAATAGTTTATGAAGTCC (SEQ ID No. 18) | 213 |
| 10 | ATATTTACAAAGGCAAGC (SEQ ID No. 19) | TGACATGATTGGTAAAAA (SEQ ID No. 20) | 180 |
|  | TGGTACATTTTCCTTTCA (SEQ ID No. 21) | CTTTATGATTGCTGGGGC (SEQ ID No. 22) | 201 |
| 11 | GGTGAAGTTTTTAATATG (SEQ ID No. 23) | CAATAGTTTATGAAGTCC (SEQ ID No. 24) | 205 |
| 12 | AATAGATAGGGAACTGCC (SEQ ID No. 25) | GTGGCTTGAGTAACAGTT (SEQ ID No. 26) | 234 |
|  | TAATGCCCACTGAAAGAA (SEQ ID No. 27) | GGCTGGTCTTGAACTCTG (SEQ ID No. 28) | 199 |

TABLE 2

SEQUENCES OF THE INTRON-EXON JUNCTIONS

| EXON | POSITION ON THE CDNA | SIZE | SEQUENCE | POSITION ON BAC AC000120 |
|---|---|---|---|---|
| 1 | 8-133 | 126 | atcaggtcag ACAGAAAACT . . . TACAAATCGG gtaagagttg (SEQ ID No. 29) (SEQ ID no. 30) | 127165-127040 |
| 2 | 134-249 | 116 | cccttctag GTAGATAAAG . . . CAGAAGACAA gtactgtttc (SEQ ID No. 31) (SEQ ID no. 32) | 126561-126445 |
| 3 | 250-393 | 144 | taatgattag GGAACGACAG . . . ATGCATGCTG gtaaatggaa (SEQ ID NO. 33) (SEQ ID no. 34) | 126228-126086 |
| 4 | 394-550 | 157 | ttttatacag GTATGGAAAA . . . AACGGATAGA gtaagttatt (SEQ ID No. 35) (SEQ ID no. 36) | 118319-118163 |
| 5 | 551-657 | 107 | acatttctag CATATAACAG . . . TAACAAACCA gtaagaatta (SEQ ID No. 37) (SEQ ID no. 38) | 117464-117357 |
| 6 | 658-815 | 157 | tttcttgtag TATGAAAAAG . . . GAAAACCTCA gtaagaaagt (SEQ ID No. 39) (SEQ ID no. 40) | 114615-114459 |
| 7 | 816-967 | 152 | tgtttttcag GCCTTCAACT . . . TGAAAAACAG gtttgcttgg (SEQ ID No. 41) (SEQ ID no. 42) | 113690-113539 |
| 8 | 968-1134 | 168 | ttccttaag ATTGAAGACC . . . GTTTCCTAAA gtaagtattt (SEQ ID No. 43) (SEQ ID no. 44) | 106414-106248 |
| 9 | 1135-1222 | 88 | gtgcttacag TGAAGAAAAT . . . TGAATACAAG gtaagctgtt (SEQ ID No. 45) (SEQ ID no. 46) | 105616-105529 |
| 10 | 1223-1429 | 207 | ttgtttttag AATCTCAGTA . . . GGAAACTAAG gtagattttc (SEQ ID No. 47) (SEQ ID no. 48) | 105038-104832 |
| 11 | 1430-1546 | 117 | tatgttgcag GCTTTACTCA . . . TACAAAACAG gtaagtatca (SEQ ID No. 49) (SEQ ID no. 50) | 93060-92942 |
| 12 | 1547-2004* | 458* | tactttgtag GCTCTGGTCG* (SEQ ID No. 51) | 92441-91984* |

*Exon 12 not entirely determined since contains Alu sequences

TABLE 3

MUTATIONS IN KRIT1

| PEDIGREE | MUTATIONS IN THE GENOMIC DNA | AMINO ACID MUTATIONS | |
|---|---|---|---|
| 6 | Deletion (A) nt 1342 Exon 10 | Amino acid changes after AA 438 | Normal (WT):IF (438) TKASPSNHKVIPVIVG . . . Mutant (MT):IF (438) TIRTAPAIIKSSLM* stop Codon |
| 10 | Missense (C→T) nt 1283 Exon 10 | Amino acid changes after AA 420 | WT:FL (420) QN . . . MT:FL (420)* stop codon |
| 18 | Insertion (C) after nt 247 Exon 2 | Amino acid changes after AA 74 | WT:ED (74) KERQWDD . . . MT:ED (74) QGTTVGR * stop codon |
| 19 | Missense (G→A) nt 261 Exon 3 | Amino acid changes after AA 79 | WT:RQ (79) WVDD . . . MT:RQ (79) * stop codon |
| 35 | Deletion (26 bp) nt 1012 Exon 8 | Amino acid changes after AA 328 | WT:EA (328) RYNLLKGFYTAPDAKL . . . MT:EA (328) SSS * stop codon |
| 41 | Missense (G→A) nt 615 Exon 5 | Amino acid changes after AA 197 | WT:NN (197) WEEAA . . . MT:NN (197) * stop codon |
| 42 | Deletion (GAAT) nt 681-684 Exon 6 | Amino acid changes after AA 217 | WT:IY (217) RMDGSYRSVELK . . . MT:IY (217) RMGHIVLLN * stop codon |
| 58 | Insertion (C) after nt 1271 Exon 10 | Amino acid changes AA 415 | WT:LQ (415) RMFLQNCQIFTKASPSNHKV . . . MT:LQ (415) HVLTQLTDIKGYKPQQS * stop codon |

REFERENCES

1. Altschul, S. F., Madden T. L., Schaffer A. A. et al. Gapped BLAST and PSI-BLAST: a new generation of protein database search programs. *Nucleic Acids Res.* 25: 3389-3402. (1997)
2. Asha H., de Ruiter N. D., Wang M. G. and Hariharan I. K. The Rap1 GTPase functions as a regulator of morphogenesis in vivo. *EMBO,* 18: 605-615 (1999)
3. Bos J. L. All in the family? New insights and questions regarding interconnectivity of Ras, Rap1 and Ral. *EMBO,* 17: 6776-6782 (1998)
4. Craig H. D., Günel M., Cepada O. et al. Multilocus linkage identifies two new loci for a Mendelian form of stroke, cerebral cavernous malformation, at 7pl(-13 and 3q25.2-27. *Hum Mol Genet* 7: 1851-1858. (1998)
5. Dubovsky J., Zabramsky J. M., Kurth J. et al. A gene responsible for cavenous malformations of the brain maps to chromosome 7q. *Hum Mol Genet* 4: 453-458. (1995)

6. Ducros A., Denier C., Joutel A. et al. Recurrence of the T666M Calcium Channel CACNA1A Gene Mutation in Familial Hemiplegic Migraine with Progressive Cerebellar Ataxia. *Am J Hum Genet*, 64: 89-98. (1999)
7. Eenson D A, Boguski M S, Lipman D J et al. GenBank. *Nucleic Acids Res* 27: 12-7 (1999)
8. Günel M., Awad I. A., Finberg K. S. et al. A Founder Mutation as a cause of cerebral cavernous malformation in Hispanic Americans. *N Eng J Med* 334: 946-951. (1996)
9. Günel M, Awad I A, Finberg K et al. Genetic heterogeneity of inherited cerebral cavernous malformation. *Neurosurgery* 38: 1265-1271. (1996)
10. Henkemeyer M., Rossi D. J., Holmyard D. P. et al. Vascular system defects and neuronal apoptosis in mice lacking ras GTPase-activating protein. *Nature* 377: 695-701. (1995)
11. Huang X., Adams M. D., Zhou H. and Kerlavage A. R. A tool for analysing and annotating genomic sequences *Genomics* 46: 37-45 (1997)
12. Johnson E W, Iyer L M, Rich S S et al. Refined Localization of the Cerebral Cavernous Malformation Gene (CCM1) to a 4 cM Interval of Chromosome 7q Contained in a Well-defined YAC Contig. *Genome Research* 5: 368-380. (1995)
13. Kiayama H., Sugimoto Y., Matsuzaki T., Ikawa Y and Noda M. A ras-Related gene with Transformation Suppressor Activity. *Cell*, 56: 77-84 (1989)
14. Knudson A G Mutation and Cancer: Statistical study of retinoblastoma; *Proc. Nat. Ac. Sci.* USA 68, 820-823 (1971).
15. Labauge P., Laberge S., Brunereau L. et al. Hereditary cerebral cavernous angiomas: clinical and genetic features in 57 French families. *Lancet* 352: 1892-258. (1998)
16. Laberge S., Labauge P., Maréchal E., Maciazek J, Tournier-Lasserve E. Genetic heterogeneity and absence of founder effect in a series of 36 non Hispano-American cerebral cavernomas families. (European Journal of Human Genetics, in Press)
17. Notelet L., Houtteville J. P., Khoury S., Lechevalier B. and Chapon F. Proliferating cell nuclear antigen (PCNA) in cerebral cavernomas: an immunocytochemical study of 42 cases. *Surg Neurol* 47: 364-70 (1997)
18. Otten P, Pizzolata G P, Rilliet B, Berney J. A propos de 131 cas d'angiomes caverneux (cavernomes) du SNC, repérés par l'analyse rétrospective de 24 535 autopsies [131 cases of cavernous angioma (cavernomas) of the CNS, discovered by retrospective analysis of 24 535 autopsies]. *Neurochirurgie* 35: 82-83 (1989)
19. Pizon V., Chardin P., Lerosey I., Olofsson B. and Tavitian A. Human cDNAs rap1 and rap2 homologous to the *Drosophilia* gene Dras3 encode proteins closely related to ras in the effector region. *Oncogene,* 3: 201-204 (1988)
20. Pizon V., Cifuentes-Diaz C., Mege R M., Baldacci G. and Rieger F. Expression and localization of Rap1 proteins during myogenic differentiation. *Eur J Cell Biol,* 69: 224-235 (1996)
21. Quarck R., Berrou E., Magnier C., Bobe R., Bredoux R., Tobelem G., Enouf E and Bryckaert M. Differential up-regulation of Rap1a and Rap1b proteins during smooth muscle cell cycle. *Eur J Cell Biol* 70: 269-277 (1996)
22. Rigamonti D, Hadley M N, Drayer B P et al. Cerebral cavernous malformations. Incidence and familial occurrence. *N Engl J Med* 319: 343-347. (1988)
23. Risau W. Mechanisms of angiogenesis. *Nature* 386: 671-674. (1997)
24. Russell D S, Rubenstein L J. Pathology of tumours of the nervous system. 5th ed. Baltimore, Md.; Williams and Wilkins: 730-736. (1989)
25. Rothbart D., Awad I. A., Lee J., Kim J., Harbaugh R., Crisculo G. R. Expression of Angiogenic Factors and Structural Proteins in Central Nervous System Vascular Malformations. *Neurosurgery* 38: 915-925 (1996)
26. Rozen S., Skaletsky H. J. Primer 3 http://wwwgenome.wi.mit.edu/genome_software/other/primer3.html (1996, 1997)
27. SerebriiskiiI., Estojak J., Sonoda G. et al. Association of Krev1/rap1a with Krit1, a novel ankyrin repeat-containing protein encoded by a gene mapping to 7q21-22 *Oncogene* 15: 1043-1049. (1997)
28. Wojnowski L., Zimmer A. M., Beck T. W. et al. Endothelial apoptosis in Braf-deficient mice. *Nature Genet* 16: 293-297. (1997)
29. Xu H P., Wang Y., Riggs M., Rodgers L. and Wigler M. Biological activity of the mammalian RAP genes in yeast. *Cell Regul* 1: 763-9 (1990)

The invention claimed is:

1. A method for genotypically diagnosing if an individual is at risk to develop cavernomas, wherein the method comprises providing a biological sample from said individual, and detecting the presence of a mutation in a Krit1 gene nucleic acid sequence present in said sample, said mutation giving rise to a truncated Krit1 protein, wherein said mutation is linked to the occurrence of cavernomas.

2. The diagnostic method as claimed in claim 1, wherein the nucleic acid sequence is genomic DNA, cDNA or mRNA.

3. The diagnostic method as claimed in claim 1, wherein said detecting comprises hybridization.

4. The diagnostic method as claimed in claim 1, wherein said detecting comprises sequencing.

5. The diagnostic method as claimed in claim 1, wherein said detecting comprises SSCP or DGGE.

6. The diagnostic method as claimed in claim 1, wherein said detecting comprises detecting the truncation of a protein.

7. The diagnostic method as claimed in claim 1, wherein all or part of the nucleic acid sequence corresponding to the Krit1 gene is amplified prior to detecting the presence of a mutation.

8. The diagnostic method as claimed in claim 7, wherein the amplification is carried out by PCR or PCR-like amplification.

9. The diagnostic method as claimed in claim 8, wherein the amplification is primed by a pair of nucleotide sequences selected from the group consisting of:
SEQ ID No. 1 and SEQ ID No. 2,
SEQ ID No. 3 and SEQ ID No. 4,
SEQ ID No. 5 and SEQ ID No. 6,
SEQ ID No. 7 and SEQ ID No. 8,
SEQ ID No. 9 and SEQ ID No. 10,
SEQ ID No. 11 and SEQ ID No. 12,
SEQ ID No. 13 and SEQ ID No. 14,
SEQ ID No. 15 and SEQ ID No. 16,
SEQ ID No. 17 and SEQ ID No. 18,
SEQ ID No. 19 and SEQ ID No. 20,
SEQ ID No. 21 and SEQ ID No. 22,
SEQ ID No. 23 and SEQ ID No. 24,
SEQ ID No. 25 and SEQ ID No. 26, and
SEQ ID No. 27 and SEQ ID No. 28.

10. The diagnostic method as claimed in claim 1, wherein said Krit1 gene mutation is detected in at least one exon of the Krit1 gene.

11. The diagnostic method as claimed in claim 1, wherein the mutation giving rise to a truncated Krit1 protein, which is detected, is selected from 1342 Del (A), 1283 C→T, 247 Ins (C), 261 G→A, 1012 Del (26 bp), 615 G→A, 681 Del (GAAt) and 1271 Ins (C).

12. The diagnostic method as claimed in claim 1, wherein the truncating mutation which is detected is responsible for the appearance of a familial form of cerebral cavernous malformation.

* * * * *

UNITED STATES PATENT AND TRADEMARK OFFICE
CERTIFICATE OF CORRECTION

| | | |
|---|---|---|
| PATENT NO. | : 7,364,844 B1 | Page 1 of 1 |
| APPLICATION NO. | : 10/019434 | |
| DATED | : April 29, 2008 | |
| INVENTOR(S) | : Tournier-Lasserve et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,390 days.

Signed and Sealed this

Twenty-eighth Day of September, 2010

David J. Kappos
*Director of the United States Patent and Trademark Office*